United States Patent [19]

Robertson

[11] 4,094,973
[45] June 13, 1978

[54] MEDICAL PROTEIN HYDROLYSATE AND PROCESS OF USING THE SAME

[76] Inventor: Harry J. Robertson, Robertson Resources Ltd., Wesley Drive, Salisbury, Md. 21801

[21] Appl. No.: 685,050

[22] Filed: May 10, 1976

Related U.S. Application Data

[63] Continuation-in-part of Ser. No. 409,145, Oct. 24, 1973, abandoned.

[51] Int. Cl.$^2$ .................... A61K 37/18; A61K 37/02; A61K 35/12
[52] U.S. Cl. ........................................ 424/177; 424/95
[58] Field of Search .................................. 424/177, 95

[56] References Cited
U.S. PATENT DOCUMENTS 2,937,974  5/1960  Ferguson .............................. 424/177

FOREIGN PATENT DOCUMENTS 576,039  5/1959  Canada .................................. 424/177

Primary Examiner—Sam Rosen
Attorney, Agent, or Firm—Newton, Hopkins & Ormsby

[57] ABSTRACT

Medical protein hydrolysate is produced from the feet of young freshly killed poultry. The protein, thus produced, is an extract of polypeptides and amino acids. It is in the form of a powder or a gel, each of which is suitable for topical application to living cells of animals and humans for aiding in healing. The process of production of the protein hydrolysate includes treating the washed and comminuted poultry feet or other source of protein with a dilute acid, preferably acetic acid, and drying under low heat conditions the resulting solution to a powder or to a gel. The process of using the protein hydrolysate including periodic topical application to a traumatized (wound) area. In the event that treatment is to be below the surface, an aqueous solution of the protein can be injected into the area to be treated.

16 Claims, No Drawings

MEDICAL PROTEIN HYDROLYSATE AND PROCESS OF USING THE SAME

REFERENCE TO RELATED APPLICATION

This is a continuation-in-part of application Ser. No. 409,145, filed Oct. 24, 1973 now abandoned.

BACKGROUND OF THE INVENTION

I have believed that there had to be a product that would create, within a traumatized (wound) area, conditions as close to fetal surroundings, as possible, so that the individual cells within this area would have the optimum chance for regeneration. Since rapidly dividing cells, in the embryo fetal complex, originate from a single fertilized cell, and then divide into specialized tissues, whether they be muscle, nerve, skin, etc., I have sought a protein source material which is readily available and inexpensive, being from immature poultry feet in which the antibodies were not well developed. Since poultry by-products were readily available, I felt this to be an ideal source.

My protein hydrolysate, described hereinafter, is believed to possess the properties which I have described above.

SUMMARY OF THE INVENTION

Briefly described, my medical Protein Hydrolysate comprises the soluble polypeptides and soluble amino acid constituents of immature animal protein such as chicken feet and its mineral content, resulting from the hydrolyzing of the animal protein with a dilute acid, preferably a weak organic acid such as acetic acid, and the subsequent drying, or concentrating, of the resulting solution.

The process comprises first cleansing the raw material, such as the feet of eight or nine week old broilers, then comminuting this raw material and subjecting it to a dilute acid, under controlled pH and temperature conditions. The resulting solution is decanted, strained or filtered and then spray dried or otherwise dewatered or concentrated to a dry powder or dried gel.

In use, the powder is topically applied to a moist open wound, or is reconstituted with water and injected, with a syringe, into the area to be treated. The gel is used for the treatment of relatively dry areas and can be reconstituted from the dry powder or from partially dried gel.

DETAILED DESCRIPTION

I preferably used the feet of freshly killed immature broilers, as my raw material and extract therefrom, polypeptides and amino acids that are lacking in antigenic properties.

In so doing, I wash and comminute the raw material, then selectively dissolve the proteins therefrom, with as little biological disruption as possible, using a dilute weak organic acid, such as acetic acid or lactic acid, as my hydrolyzing agent, supplemented by controlled extraction temperatures. Hydrochloric and phosphoric acid have also been tried with less success. By far the best acid to employ is acetic acid. The solution thus formed is a liquid product which is then dried, either by spray drying or dewatering into a dried product, which can be reconstituted into a gel.

In more detail, I use young "broiler" chicken feet as they have sufficient immature protein and are cheap and abundant. After thoroughly washing the feet in water to rid them of dirt, debris and blood, I grind the feet through a ¼ inch plate of a Hobart grinder. From ⅛ to ½ inch plates can be used; however, a ¼ inch plate appears to provide the most efficient size grind for rapid and uniform extraction of the soluble proteins.

In a separate container, I make up a water solution of glacial acetic acid by adding the glacial acetic acid to the water to produce a first dilute acetic acid solution containing from about 1% to about 1½% by weight, glacial acetic acid. Into this dilute acetic acid solution, on a one to one weight basis, I dump the ground feet so that the acid can break down or hydrolize the blood and other extraneous matter, this at room temperature, i.e., from about 70° to about 90° F. I allow the comminuted feet and dilute acetic acid solution to work overnight, i.e., 8 to 12 hours, stirring it periodically so that it is well mixed. I then wash or flush the mixture with fresh water until the comminuted feet mix is clear of debris. This initial treatment or pretreatment with acetic acid solution is to remove blood, free fats and serum.

I then make up another mixture of glacial acetic acid and water so as to provide a second solution having a pH 4.6. The pH may run from pH 6.5 to pH 3.6 if desired. However, I have found that, where I have used these extreme ranges, resulting protein material is not as effective. The washed comminuted feet mix is then added to this second solution in a one to one ratio by weight and the resulting mix is heated to a temperature of between 130° and 140° F and constantly stirred for about 30 – 40 minutes, but it can be comingled and heated for a shorter period of time, with a decrease in yield.

This solubilized mixture is then decanted or drawn off and sent through a centrifuge to remove most of the fat and particulate matter. The defatted centrifuged solution is then passed through a filter. So far, I have found that the best filter bed to use is "Speed Flow" diatomaceous earth, though I am sure there are other filters that would be equally effective.

I next allow the dissolved protein solution to solidify. I then skim off the remaining fats. To again solubilize this gelled protein, I once again heat it to 100° – 120° F so that it can be pumped. This mixture (solution) of amino acids and polypeptides generally runs from 4% – 9% solids. If I want to make a gel of it, I dry the solidified (gelled solution) by low temperature air drying and reconstitute it when I need it by again bringing the solubilizing water up to 100° – 130° F.

If desired, another or second extraction, using the second acetic acid solution (pH 4.6) on a pound for pound basis of the previously extracted ground feet and acetic acid solution. I extract for 30 minutes at 140° – 155° F and blend this mixture in with the other filtered and clarified protein solution, after first going through the same defatting and clarifying steps as on the first extraction. I have not found that this second product is as good as the first extraction as I think there is too much denaturation of the proteins, therein.

To produce the dry powder, the resulting solution is spray dried. The powder has an average particle size from about 1 to about 20 microns.

The same procedure was followed with a solution of lactic acid, also diluted until the pH was about 4.6. The resultant powder was effective, but to a lesser extent than that produced with acetic acid. As is conventional, other weak organic acids could be used with similar results. The same occurred when hydrochloric and phosphoric acid were used.

A better understanding of the present invention will be had by reference to the following examples.

EXAMPLE I 100 pounds of frozen poultry feet, obtained from freshly killed commercial broilers, 8 to 9 weeks old, grown and processed in Maryland, U.S.A., were washed with water to remove coarse debris, dirt and blood. They were then ground using a Hobart Grinder with a ¼ inch plate and this comminuted material was immersed in 100 pounds of a 1% solution of aqueous glacial acetic acid for a period of 10 hours at room temperature. The mixture was stirred at least once per hour to maximize the area exposed to the dilute acetic acid.

Next the solution was drained from the comminuted feet by being poured onto a 1/32 inch mesh screen. The material on the screen was then washed with water until the wash water was clear. This resulted in 87 pounds of cleansed comminuted or ground broiler or poultry feet.

A first extraction was made by mixing glacial acetic acid and water to produce a resulting solution having about 1% by weight, glacial acetic acid.

To 87 pounds of the first extraction solution was added the 87 pounds of cleansed comminuted poultry feet. The pH of the mix was then adjusted to a pH of 4.6 by the addition of glacial acetic acid. This mixture was then constantly stirred and brought to a temperature of about 130° F and maintained within the range of about 130° to about 140° F for about ½ hour so as to dissolve the soluble protein from the ground material.

This hot solubilized mixture was then passed through a milk centrifuge so that the fat was discharged from the solution and the solids or non-solubilized material removed therefrom.

Thence, the centrifuged solution was filtered by being passed through diatomaceous earth (Speed Flow — a Dow Chemical [Grefco] product). At this stage the solution was a clear solution containing approximately 5.7 pounds of the polypeptide and amino acids mix.

While still in its liquid state, the clear solution at a temperature of from about 100° to about 120° F was passed through a spray drier. The inlet temperature of the air was about 250° F and the outlet temperature was about 120° F. The resulting non-antigenic protein hydrolysate powder, being hydroscopic, was then immediately placed in an air tight, moisture impervious container so that it would not cake.

The resulting powder assayed as follows:

| pH | 4.6 |
|---|---|
| water | 7.9 |
| Total N | 15.73 |
| ash | 6.10 |

Amino acid distribution -

| aspartic acid | 5.51 |
|---|---|
| glutamic acid | 10.24 |
| histidine | 0.81 |
| lysine | 3.80 |
| argenine | 8.01 |
| hydroxylysine | 1.19 |
| hydroxyproline | 10.14 |
| threonine | 2.26 |
| serine | 2.86 |
| tyrosine | 0.73 |
| glycine | 23.41 |
| ½ cystine | 0.32 |
| proline | 11.83 |

-continued

| alanine | 9.14 |
|---|---|
| valine | 2.43 |
| methionine | 1.24 |
| leucine | 3.00 |
| isoleucine | 1.76 |
| phenylalanine | 2.23 |

EXAMPLE II

The procedure of Example I was repeated but instead of spray drying, the filtered solution was dried in dry air at a temperature of from 65° to 75° F, until it contained about 5%, by weight, moisture.

The resulting protein hydrolysate material weighed 6.1 pounds and was placed in an airtight, moisture impervious container.

The material was later mixed with water to produce various samples of gels containing from about 15% to about 30%, by weight, of the material. The water was preheated to from about 120° to about 130° F and the material added to the warm water. The gels were kept under refrigeration.

In Examples I and II a Sharpless centrifuge or cream separator with fixed parts was used. A Bowen spray dryer was used in Example I.

In the procedure of the protein hydrolysate described above, i.e., by extracting the polypeptides and amino acids through the use of acetic acid as a solvent for the extracted proteins, the proteins are broken down from their complex protein structures to the simpler structures. It is important, for best results, that the solids, i.e., minerals, which precipitate out as the filtered hydrolyzed protein is dewatered and cooled be retained in the resulting product. Protein hydrolysate, without such minerals, while causing excellent repair of a wound, may result in concomitant hyperplasia which should be debrided to bring it in line with adjacent tissue. Thereafter, the wound will slowly continue to repair.

In other words, I have found that it is not desirable to remove the precipitated minerals which precipitated out as the extracted (solubilized) proteins lose moisture and that it is not desirable to filter the product after it is in concentrated form. When the non-precipitated mixtures of Examples I and II were used, the hyperplasia of regenerating tissue disappeared and remarkable regrowth of not only muscle tissue, but skin and nerve tissue, also, regenerated and returned to its normal position and contour and function, indicating that it restored memory to the tissues.

TREATMENT USING MY MEDICAL PROTEIN HYDROLYSATE

My protein hydrolysate is particularly useful for the treatment of burns, particularly third degree burns. The dry powder is sprinkled over the effected area and combines with the moisture in the tissue to provide a protective cell stimulating coating. The gel is preferably used for first and second degree burns, where a relatively dry area is involved. Pain is usually stopped in three to five minutes after application to the effected area. I have found it preferable to apply a sprinkled layer of dry powder or gel to the burned area about every third day.

In the case of third degree burns, the powder allows for the fiberblasts or regenerative cells to continue to grow out from the center and edges of the wound so that skin grafting is materially reduced or entirely eliminated. Furthermore, the new skin even appears to be formed from normal cells and hair actually grows from the new skin in a normal way.

In most cases of wounds in animals treated with my material, either spray dried or in gel form, bacterial infections have generally been eliminated after the first 3 days, and in all cases, infection appeared to be eliminated at the end of the seventh day (end of second application). This has been demonstrated with gas gangrene (clinically), massive disruptive wounds resulting from auto and other traumatic disruptions of the skin and underlying muscle, nerve and vascular tissues.

When using my material topically applied, either in spray dried powder or gel form, the hyperplasia of regenerating tissue disappeared and remarkable regrowth of not only muscle tissue, but skin and nerve tissue, also, regenerated and returned to its normal position and contour and function, indicating that it restored memory to the tissues.

Bed sores which have existed for some time have healed quite well after treatment with my material. Indeed, even cells which appeared to have died around a wound were restored to normal.

COMPARATIVE TEST

To demonstrate the importance of using immature animal tissue and particularly immature poultry feet, the following test was run. Four cats of like weight, maturity and state of health were operated on and three muscles of the upper right thigh were severed: the Bicepts femoris, the Vastus lateralis and the Semitendinosus. Each cat was treated with an agent topically applied to cover the wound twice a week until all wounds healed.

The first cat was treated with protein hydrolysate prepared according to Example II above. Its wounds healed in 21 days without complications. It walked without a limp in 7 days.

A second cat, treated with a protein hydrolysate prepared in an identical manner from the feet of chicken about 1 year old. Healing took 33 days and hyperplasia developed on the 8th day. Normal walking occurred only on the 15th day.

A third cat was treated with a prior art protein hydrolysate, hydrolysed casein, a Borden product. It developed hyperplasia on the 7th day and a secondary infection, both of which persisted until final healing at 33 days. This cat limped until final healing.

The fourth cat, treated with the broad spectrum antibiotic 5-Nitro-2-fureldehyde semi-carbazone ("FURACIN," a product of Eaton Laboratories). Healing took 33 days. A lesser amount of hyperplasia was noted and the cat walked with a limp for the entire period.

The third and fourth cats also exhibited progressive atrophy of the muscles posterior to the incision continuing until the femur could be palpitated.

This test demonstrates the effectiveness and advantages of protein hydrolysate prepared according to the present invention and particularly speed of recovery, lack of infection, absence of hyperplasia and full return of muscle function.

It is thus seen that the therapeutic agent of the present invention, i.e., my medical protein hydrolysate, is a hydroscopic mixture of polypeptides and amino acids. It appears to have the fantastic ability to create, around a wound area, conditions that allow true tissue regeneration, this in the total absence of antibodies, even in the most critically infected wounds.

Preferably, the wound is heavily covered with my powder or gel. When powder is used, the area must be moist so that the powder can stick. No adverse tissue reaction has been observed in any treatment using my Protein Hydrolysate.

It is desirable to cover the wound with a non-adhering dressing (Telfa) to keep the powder/gel in contact with the wound. The treatment of the wound with my material should be repeated every 3 or 4 days.

What is claimed is:

1. A therapeutic agent comprising a non-antigenic, protein hydrolysate having polypeptides and amino acids derived by:
   comminuting the immature poultry feet and washing them;
   commingling said comminuted immature poultry feet with a dilute, mild organic acid at a pH between 6.5 and 3.6 at an elevated temperature up to 155° F;
   removing the fat constituent; and
   removing the solubilized protein and dissolved minerals at the elevated temperature.

2. The therapeutic agent as claimed in claim 1 wherein said elevated temperature is between 130° F and 140° F.

3. The therapeutic agent as claimed in claim 1 wherein said poultry feet are derived from chickens; not more than 9 weeks old.

4. The therapeutic agent as claimed in claim 1 wherein said mild organic acid is acetic acid.

5. The therapeutic agent as claimed in claim 1 wherein in the step of comminuting the immature poultry feet and washing them, said poultry feet are ground and pretreated with a mild organic acid solution from 1 to 1½ % by weight acid at from 70° to 90° F for from 8 to 12 hours, after which pretreatment the poultry feet are washed with water.

6. The therapeutic agent as claimed in claim 1 wherein said removing the fat constituent step includes cooling the solution and separating out the fat layer.

7. The therapeutic agent as claimed in claim 6 wherein said agent is a dehydrated gel and is derived by reheating the cooled solution and air drying of the reheated solution to form this dehydrated gel.

8. The therapeutic agent as claimed in claim 1 wherein said agent is a powder and is derived by spray drying the resultant solution from which the fat material has been removed.

9. The therapeutic agent as claimed in claim 1 wherein said removing the precipitate step includes decanting.

10. The therapeutic agent as claimed in claim 1 wherein said removing the precipitate step includes filtering through diatomaceous earth.

11. The process of treating damaged higher animal tissue for therapeutic purposes comprising the applying to said tissue an effective amount of a non-antigenic protein hydrolysate as claimed in claim 1.

12. The process of claim 11 wherein said protein hydrolysate is an aqueous gel.

13. The process of claim 12 wherein said tissue includes an open wound and said protein hydrolysate is a dry powder covering said wound.

14. The process of claim 11 wherein said protein hydrolysate is injected into a tissue.

15. A therapeutic agent comprising, a non-antigenic, protein hydrolysate having a mixture of polypeptides and amino acids therein, said protein hydrolysate being the soluble constituent derived from immature poultry feet which have been hydrolized by mild acid hydrolysis.

16. A therapeutic agent comprising, a non-antigenic, protein hydrolysate derived by mild acid hydrolysis from immature poultry feet in which the anti-bodies are not fully developed.

* * * * *